United States Patent [19]

Waite

[11] Patent Number: 4,687,740

[45] Date of Patent: Aug. 18, 1987

[54] DECAPEPTIDES PRODUCED FROM BIOADHESIVE POLYPHENOLIC PROTEINS

[75] Inventor: J. Herbert Waite, Collinsville, Conn.

[73] Assignee: University of Connecticut Research & Development Corp., Farmington, Conn.

[21] Appl. No.: 820,143

[22] Filed: Jan. 21, 1986

Related U.S. Application Data

[62] Division of Ser. No. 587,132, Mar. 7, 1984, Pat. No. 4,585,585.

[51] Int. Cl.⁴ .............................................. C12P 21/06
[52] U.S. Cl. ..................................................... 435/69
[58] Field of Search .................................. 435/69, 70

[56] References Cited

U.S. PATENT DOCUMENTS 4,496,397 1/1985 Waite .................................. 106/161

OTHER PUBLICATIONS

Waite et al., Science vol. 212, pp. 1038–1040 (1981).
Waite, Journal of Biological Chemistry vol. 258, No. 5, pp. 2911–2915, Mar. 10, 1983.

*Primary Examiner*—Lionel M. Shapiro
*Attorney, Agent, or Firm*—Jones, Day, Reavis & Pogue

[57] ABSTRACT

Methods are described for the preparation and isolation of novel decapeptides of the formula:

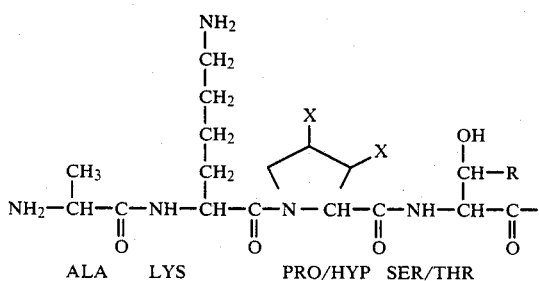

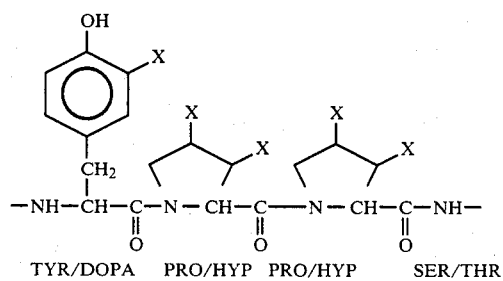

-continued

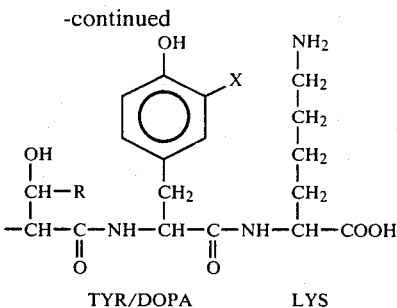

wherein each X is independently selected from the group comprising hydroxyl and hydrogen, wherein each R is independently selected from the group containing hydrogen and methyl, from bioadhesive polyphenolic proteins which comprise:

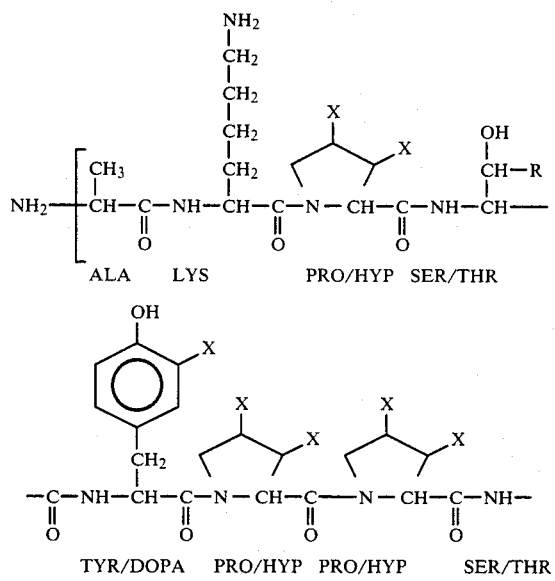

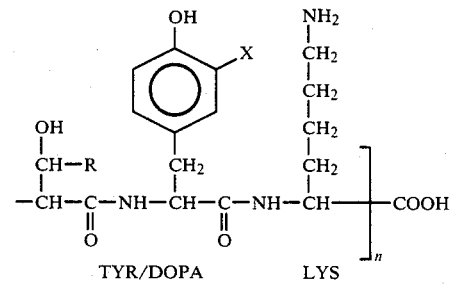

wherein n is a whole number from about 60 to about 100, wherein each X is independently selected from the group comprising hydroxyl and hydrogen, and wherein each R is independently selected from the group comprising hydrogen and methyl.

Such decapeptides may be used to construct large polyphenolic molecules comprising from about 1 to about 1000 decapeptide repeating units and wherein the linking group is selected from the group comprising amino acid, oligopeptide and bifunctional spacer.

6 Claims, No Drawings

DECAPEPTIDES PRODUCED FROM BIOADHESIVE POLYPHENOLIC PROTEINS

This is a divisional of co-pending application Ser. No. 587,132 filed on Mar. 7, 1984, now U.S. Pat. No. 4,585,585, issued Apr. 29, 1986.

BACKGROUND OF THE INVENTION

1. Field of the Invention

The present invention relates to bioadhesive polyphenolic proteins derived from several species of the mussel genus Mytilus. These polyphenolic proteins, which contain a sequence of repeating decapeptides, exhibit unusually superior adhesive capabilities toward a variety of surfaces including surfaces submerged in water.

2. Description of the Prior Art

Adhesives well known in the art are generally applied to dry surfaces in order to effect a strong bond. The vast majority of adhesives bind dry surfaces more strongly than the same surfaces when wet. For example, resorcinol-formaldehyde polymers which are useful in making waterproof, boil-proof plywood and particle board cannot be applied to surfaces underwater due to the dispersive effect of water on the monomers (resorcinol and formaldehyde). For these compositions to form a strong bond, the monomers must be mixed, set, and cured at about 10 to about 50% relative humidity at temperatures equal to or exceeding about 20° C. Thus, present adhesive technology is stymied by the presence of water on substrates: water competes with the adhesive for surface area on which to bind. In addition, for many adhesives, water tends to hydrolyze or plasticize the adhesive.

Methods for the isolation of polyphenolic proteins from the mussle genus Mytilus are known in the art, and are described in the article of Waite and Tanzer, *Science* 212, 1038 (May 29, 1981). Heretofore, however, no method for the preparation and isolation of decapeptides from polyphenolic proteins have been known.

Thus, it is an object of this invention to provide a method for the preparation of repeating decapeptides from said bioadhesive proteins.

It is yet another object of the present invention to provide decapeptides for preparing larger bioadhesive molecules useful in binding surfaces in the presence of water.

SUMMARY OF THE INVENTION

The foregoing and other objects, advantages, and features of this invention may be achieved by the use of bioadhesive polyphenolic proteins which comprise:

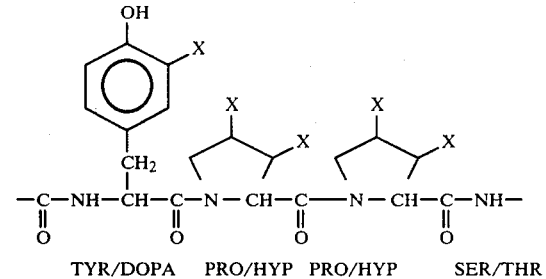

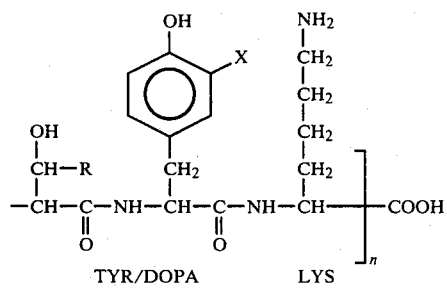

wherein n is a whole number from about 60 to about 100, wherein each X is independently selected from the group comprising hydroxyl and hydrogen and wherein each R is independently selected from the group comprising hydrogen and methyl.

Digestion of the polyphenolic proteins in trypsin in the presence of a neutral or slightly basic buffer results in decapeptides of the formula:

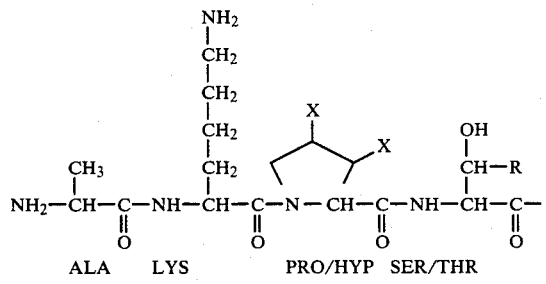

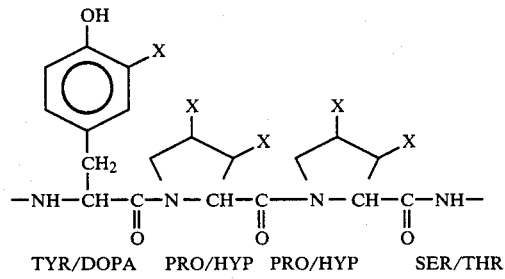

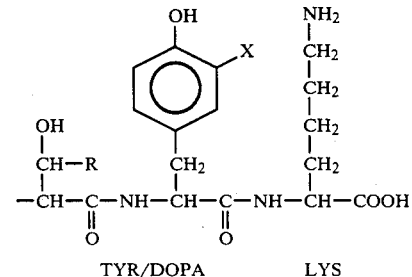

wherein each x is independently selected from the group comprising hydroxyl and hydrogen and wherein each R is independently selected from the group comprising hydrogen and methyl.

Such decapeptides may be used as "building blocks" in the construction of larger polyphenolic molecules possessing the adhesive capabilities of the native bioadhesive protein, comprising from about 1 to about 1000 decapeptide repeating units and wherein the linking group comprises amino acid, oligopeptide or bifunctional spacer.

DETAILED DESCRIPTION OF THE INVENTION

Bioadhesive polyphenolic proteins are characterized by a very low aqueous dispersive effect probably due, at least in part, to the high amounts of hydroxyproline (HYP) and 3,4-dihydroxyphenylalanine (DOPA) present in the proteins. Such bioadhesive proteins are further characterized by their low solubility at neutral or slighly basic pH. In addition, such proteins behave as polymers and adhere to teeth and bone surfaces as well as wood, glass, iron, steel, slate, and so forth under water (at about 300 to about 1000 pounds per square inch). Such bonds appear to be durable in the presence of water for years.

These bioadhesive proteins may be isolated and purified from dissected phenol glands of mussels. Because bioadhesive proteins exhibit a rather low solubility at neutral pH, these proteins may be purified initially by extracting impurities, including extraneous proteins, with large amounts of a neutral or slightly basic salt buffer followed by gentle centrifugation. The neutral or slighly basic salf buffer contains various protease inhibitors to prevent premature degradation of the bioadhesive proteins as well as cyanide which prevents enzymatic oxidation of the DOPA residues prevalent in the bioadhesive proteins. It is important to use a gentle first centrifugation to prevent the irreversible coalescence of insoluble proteins, which include the bioadhesive proteins. After centrifugation, the insoluble materials are re-extracted with an acidic solution, most preferably acetic acid, in which the polyphenolic proteins are very soluble. It should be noted that a high yield purification of the bioadhesive proteins is difficult due to the extensive adsorption of the proteins to surfaces.

Bioadhesive proteins may be purified by a combination of ion exchange and gel filtration on low surface-energy chromatographic media. Ion exchange on sulfonylpropyl-Sephadex provides a most effective purification step. Gel filtration of bioadhesive proteins using a variety of chromatographic materials and buffers generally result in a very low or negligible yield. Yield can be improved on Sephadex if an elution buffer with a low pH (in the range of about 2 to about 4) and a cationic detergent are used. Although recovery from phenyl-Sepharose 4B is excellent, this material provides a limited fractionation range and is generally not preferred for purifying the bioadhesive proteins. The apparent molecular weight of the bioadhesive proteins, as determined by polyacrylamide gel electrophoresis in the presence of cetylpyridinium bromide, is estimated to be about 120,000 to about 140,000.

When the bioadhesive proteins are treated with clostridial collagenase, the molecular weight is reduced to between about 110,000 and about 130,000. Collagenase digestion may be performed in a salt buffer solution with collagenases of varying purity. It is preferred to use collagenase of high purity in a neutral on slightly basic buffer, most preferably a borate-salt buffer. The resultant collagenase-resistant fragments contain most of the HYP and DOPA of the original bioadhesive proteins.

Collagenase-resistant fragments are rapidly degraded by trypsin into decapeptides, the repeating unit in the native protein. Trypsin degradation of the collagenase-resistant fragments may be performed in a salt buffer at neutral or slighly basic pH. Again, the use of a borate-salt buffer is especially preferred. At the termination of the trypsin digestion, the decapeptides may be purified by gel filtration dialysis, or a combination of known purification techniques.

Alternatively, trypsin digestion may be performed on isolated bioadhesive proteins, producing the same decapeptides, without first treating the bioadhesive proteins with clostridial collagenase. Trypsin degradation is again performed in a salt buffer at neutral or slighly basic pH, with the use of a borate-salt buffer being especially preferred. At the termination of the trypsin digestion, the decapeptides may be purified from the collagenase-labile fragments by gel filtration dialysis, or by a combination of known purification techniques.

These decapeptides comprise:

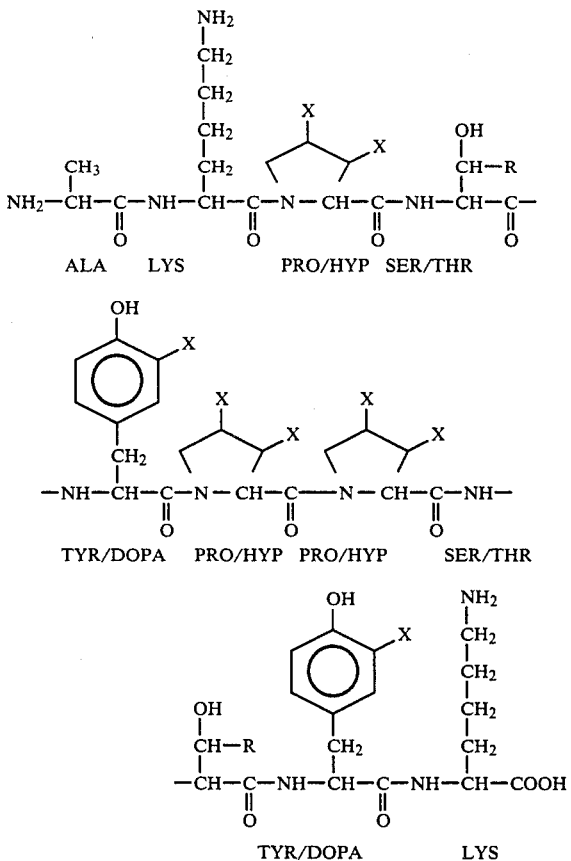

wherein each X is independently selected from the group comprising hydroxyl and hydrogen and wherein each R is independently selected from the group comprising hydrogen and methyl.

These decapeptides. which are principally responsible for the bioadhesive properties of the bioadhesive proteins, may be repeated from 60 to about 100 times in bioadhesive polyphenolic proteins isolated from the marine mussel. Because of the prevalence of hydroxyl-substituted phenyl groups in the decapeptides, the parent bioadhesive protein is often referred to as a "polyphenolic" protein.

It is believed that the large amounts of hydroxyproline (HYP) and 3,4-dihydroxylphenylalanine (DOPA) as well as the numerous hydroxyl groups in the polyphenolic proteins are largely responsible for the non-dispersive properties of the protein.

It is possible to construct large polyphenolic molecules possessing the adhesive capabilities of the naturally occurring bioadhesive proteins, comprising from about 1 to about 100 decapeptide repeating units and wherein the linking group comprises amino acid, oligopeptide and bifunctional spacer. Known bifunctional compounds may be used to induce the polymerization of the decapeptides. Virtually any bifunctional compound in which both functionalities react with or become ionically associated with hydroxyl groups, amine groups of carboxyl groups may be used. While aqueous salt buffers at neutral or slightly basic pH may be used as a reaction medium, the use of organic solvents may likewise be used. The reaction of the decapeptides and bifunctional linking group is continued at a temperature, and for a time period necessary to substantially complete the polymerization.

Classical methods of protein synthesis may also be used to link decapeptides to form larger polyphenolic molecules. Methods contemplated herein include well-known blocking, activating, linking, and deblocking sequences for peptide synthesis. While no linking group is necessary in such syntheses, linking groups of amino acids and oligopeptides may be used.

Amino acids which may be used as linking groups in the construction of large polyphenolic molecules comprise any of the naturally occurring L-amino acids, as well as other amino acids such as ornithine, homocysteine, citrulline, 3-aminotyrosine, and the like.

Oligopeptides which may be used as linking groups comprise any di-, tri-, tetra- or penta-peptides and higher peptides that may be readily synthesized or available from commercial sources. Examples of oligopeptides include (ala-cys-ala), (ala-lys)$_3$, (ala-lys-pro)$_4$, (pro-hyp-gly)$_5$, and the like.

Bifunctional spacers which may be used as linking groups comprise aliphatic or aromatic dialdehydes, imido esters, diisocyanates, aryl and alkyl dihalides, dimaleimides, and the like. The dialdehydes may be of the type: OHC—R—CHO, wherein R is selected from the group comprising lower alkyl, aryl or substituted aryl. Examples of suitable dialdehydes include glutaraldehyde, malonaldehyde, glyoxal, 1,4-butanedialdehyde, and the like. Useful imido esters comprise:

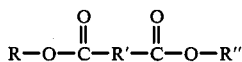

wherein R, R' and R" are independently selected from the group comprising lower alkyl, aryl or substituted aryl. Examples of suitable imido estes include dimethyl malonimidate, dimethyl suberimidate and dimethyl adipimidate.

Useful diisocyanates comprise: O=C=N—R—C=N=O, wherein R is selected from the group comprising lower alkyl, aryl and substituted aryl. Examples of suitable diisocyanates include pentamethylene diisocyanate, hexamethylene diisocyanate, heptamethylene diisocyanate, and toluene-2,4-diiosocyanate. Useful aryl dihalides comprise:

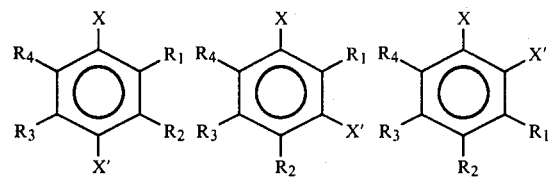

wherein X and X' are independently selected from the group comprising F, Cl, Br, and I and $R_1$, $R_2$, $R_3$, and $R_4$ are selected independently from the group comprising lower alkyl, aryl or substituted aryl. Examples of suitable aryl dihalides include p-dibromobenzene, o-bromoiodobenzene 2,4-dibromotoluene and the like. Useful alkyl dihalides comprise: X—R—X', wherein X and X' may be independently selected from the group comprising F, Cl, Br and I; and R may be alkyl or substituted alkyl. Examples of alkyl dihalides include 1,2-dibromoethane, 1,3-dibromopropane, methylene bromide, methylene iodide and the like.

Dimaleimides which may be used comprise:

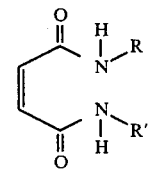

wherein R and $R_1$ are independently selected from the group comprising hydrogen, lower alkyl or aryl. Examples of suitable dimaleimides include bis(N-maleimidomethyl)ether and the like.

EXAMPLE 1

Isolation and Purification of Bioadhesive Polyphenolic Proteins

Prior to the isolation of bioadhesive polyphenolic proteins, mussel phenol glands were isolated and extracted, generally in accordance with the method described by Waite and Tanzer, Science 212, 1038 (May 29, 1981). The shells of fresh live mussels (Mytilus edulis) were opened by cutting the anterior and posterior adductor muscles with a scalpel. The animals were then killed by cardiac puncture and the foot from each animal was amputated at the base and placed on ice. Mussel feet in lots of 30 were transferred to clean glass plates (20×20×0.2 cm) and frozen over dry ice. The phenol gland which can readily be located near the foot tip was dissected from each foot after stripping off the pigmented epithelium. The phenol glands from 450 mussel feet were suspended in 750 ml. buffer containing 1 M NaCl, 0.05 M tris (pH 7.5), 1 mM phenylmethylsulfonylfluoride, 10 mN N-ethylmaleimide, 0.025 M ethylenediamine tetraacetic acid and 1 mM potassium cyanide and homogenized in ground glass tissue grinders at 4° C. The homogenates were lightly centrifuged for 5 min. at about 2500 X g and the supernatants were discarded. The pellets were resuspended in cold 0.8 M acetic acid (150 ml) and rehomogenized briefly with tissue grinders. The second homogenate was centrifuged for one hour at about 40,000 X g and about 4° C. The supernatant was rich in polyphenolic proteins.

Polyphenolic proteins were isolated in two steps. First, the acetic acid supernatant was dialyzed against a large volume of 0.8 M acetic acid. The nondialyzable fraction was adjusted with guanidine-HCl to a conductance of 30 mMHO and a final composition of 5.5% guanidine-HCl, 0.8 M acetic acid and 0.001% (v/v) Triton X-100 (Buffer A). This was applied to a column of sulfonylpropyl-Sephadex C-50 (25×1 cm) pre-equilibrated at about 20° C. with a buffer of the same composition. Polyphenolic proteins were eluted from the column at a buffer conductance from about 40 to about 60 mMHO by using a linear gradient produced by mixing the first buffer (A) with 20% guanidine hydrochloride, 0.8 M acetic acid and 0.001% Triton X-100. Yields of polyphenolic proteins were substantially better when chromatographed on sulfonylpropyl-Sephadex possessing manufacturer's four-digit batch numbers than when chromatographed on sulfonylpropyl-Sephadex with manufacturer's five-digit designations. Following ion exchange, peak fractions of polyphenolic proteins were dialyzed against 0.8 M acetic acid to remove detergent and guanidine-HCl. Further purification was achieved on columns (both 65×2 cm) of Sephadex G-200 and Phenyl-Sepharose 4B eluted with 0.3 M ammonium acetate (pH 4.0) and 0.01% cetylpyridinium bromide, and 3% guanidine in 0.8 M acetic acid, respectively. Numerous other buffers and chromatographic media were tested, but recoveries of polyphenolic proteins were, in most instances, too low to merit further description.

EXAMPLE 2

Trypsin Digestion of Polyphenolic Proteins

For trypsin digestion, 5 mg of the polyphenolic proteins were dialyzed against 0.01 M sodium borate (pH 8.5) with 3 M urea and 0.01 mM $CaCl_2$. Trypsin was added at an enzyme to substrate ratio of about 1 to 100, and the reaction was stirred under oxygen-free nitrogen at 25° C. for 24 hours. At the end of this period, the reaction was terminated by adding a few drops of glacial acetic acid (to pH 4) and flash evaporated to about 0.5 mL. Sample volume was adjusted to 1 mL with 0.2 M acetic acid and centrifuged to remove insoluble material. The supernatant was applied to a column of Sephadex LH 60 (80×1.5 cm) eluted with 0.2 M acetic acid. Fractions were assayed for ninhydrin-positive material and DOPA. The material containing both DOPA and amines was pooled, flash evaporated and resuspended in 0.2M pyridine acetate (pH 3.1). This sample was applied to a Sephadex SP-25 column (20×1 cm) eluted with a linear pH gradient ranging from pH 3.1 to pH 5.0 (2.0 M pyridine acetate). Fractions were tested as described above. Again, the DOPA-rich, ninhydrin-positive peak fractions were flash evaporated and purified on a column of Sephadex LH 20 (80×1.5 cm) eluted with 0.2 M acetic acid. This peak was flash evaporated to dryness and stored at −20° C.

Trypsin digestion of the polyphenolic proteins is extensive and rapid. Under the conditions used, the proteins completely disappeared within 5 min. of the addition of trypsin as determined by gel electrophoresis. Fractionation of the tryptic digest was achieved using gel filtration to Sephadex LH-60, which removes trypsin from the peptides, followed by ion exchange on Sephadex SP-25 with a pyridine acetate gradient (the latter method being recommended for basic aromatic peptides). About 75–80% of the ninhydrin-positive material eluting from SP-Sepadex can be ascribed to the DOPA-containing peak. Moreover, nearly 95% of the DOPA and 80% of the proteins, originally applied to SP-Sephadex are recovered in the major DOPA-rich peak. This material was further purified by passage through Sephadex LH-20. The tryptic decapeptides resemble the polyphenolic proteins in containing the same group of amino acids that predominate in the latter, namely HYP, THR, SER, PRO, ALA, DOPA, TYR, and LYS. In the tryptic decapeptides, however, DOPA and HYP are significantly enriched, whereas LYS, PRO and TYR are reduced. The tryptic decapeptides were homogeneous on 12% acrylamide gels in 3 M urea and 5% acetic acid but were visualized by DOPA staining since they could not be fixed for protein staining. Molecular weight of the decapeptides in cetylpyridinium bromide gel electrophoresis was estimated to be about 6500. Peptide homogeneity was also suggested by thin layer chromatography on cellulose in 1.5% formic acid and thin layer electrophoresis in 5% acetic acid. Since borate strongly complexes DOPA at pH 7–9, it has the property of introducing additional negative charges into the decapeptides. Heterogeneity of the decapeptides (2 spots) in borate suggests variation in the degree of TYR to DOPA conversion.

Sequenator analysis (35 cycles) of the tryptic decapeptides revealed it to be a mixture of decapeptides (molecular weight of about 1400) comprising:

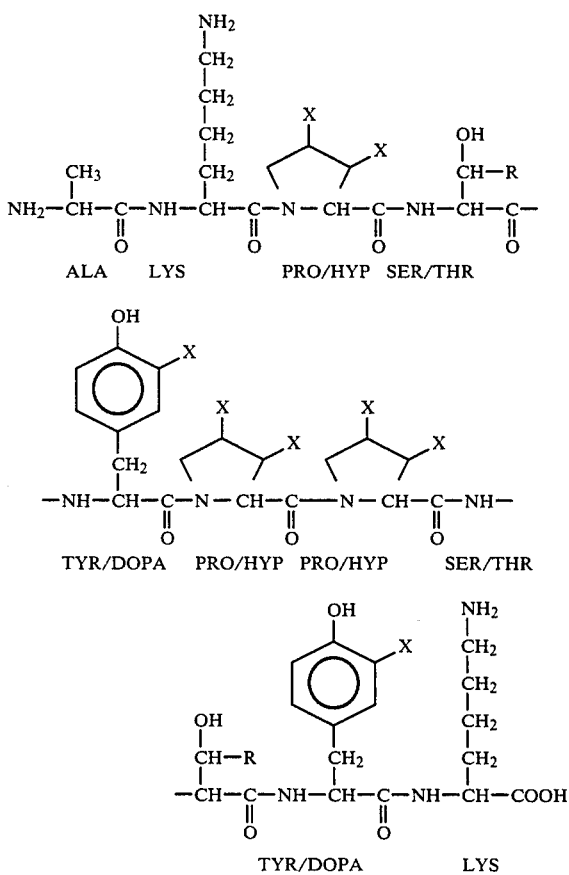

wherein each X is independently selected from the group comprising hydrogen and hydroxyl and wherein each R is independently selected from the group comprising hydrogen and methyl.

EXAMPLE 3

Enzymatic Digestion of Polyphenolic Proteins With Clostridial Collagenase

As described above, polyphenolic protein may be enzymatically digested to prepare novel decapeptides by the use of trypsin alone. In addition, purified polyphenolic proteins may be enzymatically digested to prepare novel decapeptides with the successive use of two proteases—clostridial collagenase and trypsin. This example describes the degradation of the polyphenolic proteins with clostridial collagenase.

Collagenase used was of high specific activity (7 X $10^{-11}$ moles leucine released/min/mg) and had no detectable endopeptidase activity with casein as a substrate. Polyphenolic proteins (1 mg) were dialyzed against 0.1 M sodium borate pH 8.0 with 0.01 mM $CaCl_2$ under nitrogen. Collagenase was added at an enzyme to substrate ratio of 1:250. The reaction mixture was incubated at 35° C. under continuous stirring and 50 microliter aliquots were periodically removed for electrophoretic analysis. Collagenase activity was terminated by lowering aliquot pH to 4.0 with acetic acid.

Collagenase treatment of polyphenolic proteins results in only limited degradation. Only about 8% of protein was attacked, leaving entirely intact a fragment with $M_r = 120,000$. This collagenase-resistant fragment has an amino acid composition similar to that of the original protein but is noticeably reduced in glycine and proline. Clostridial collagenase selectively cleaves proline-glycine linkages in the polyphenolic proteins.

EXAMPLE 4

Polymerization of Bioadhesive Decapeptide Using a Bifunctional Linker

Decapeptides may be polymerized using a glutaraldehyde linking group as follows. Decapeptides (4 mg) prepared from the isolated polyphenolic protein by trypsin degradation, as described above in Example 2, are mixed in sodium acetate (1 ml, 0.2M, pH 7). Aueous glutaraldehyde (1 ml, 25% w/v) is added in a dropwise fashion. The mixture is stirred vigorously for about 90 minutes at room temperature. At the end of this time, the mixture is dialyzed against 1000 volumes of distilled water at about 4° C. for about six hours. The nondialyzable fraction is freeze-dried. The polymerization is confirmed by gel electrophoresis of the product in the presence of cetylpyridinium bromide.

While the foregoing is intended to illustrate methods for the isolation of bioadhesive polyphenolic proteins and the preparation of decapeptides therefrom as well as the polymerization of the decapeptides, these examples are not intended nor should they be construed as a limitation on the invention. As one skilled in the art would understand, many variations and modifications may be made in these processes and compositions that fall within the spirit and scope of this invention.

I claim:

1. A method for the preparation of decapeptides of the formula:

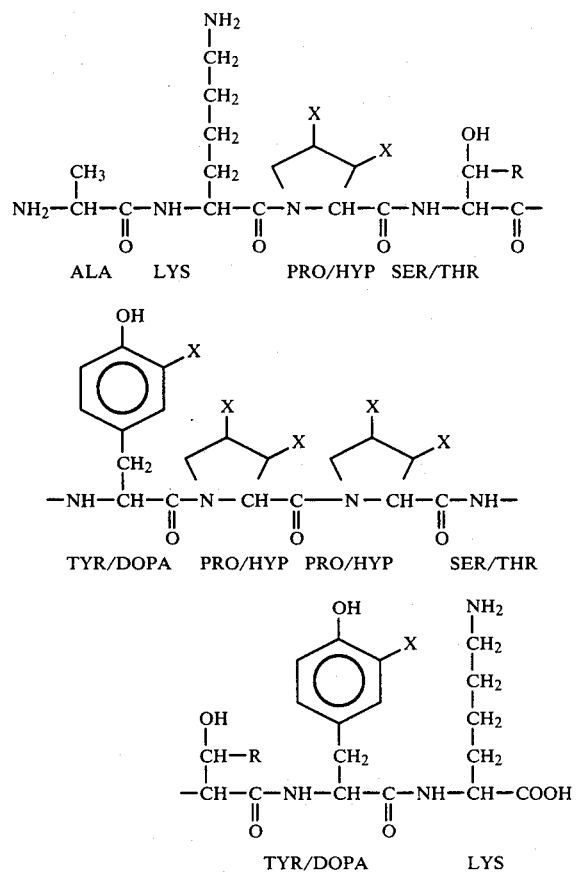

wherein each X is independently selected from the group consisting of hydroxyl and hydrogen, wherein each R is independently selected from the group consisting of hydrogen and methyl which comprises the steps of:
  (a) isolating bioadhesive proteins from mussel phenol glands;
  (b) enzymatically digesting said bioadhesive protein; and
  (c) recovering said decapeptides.

2. A method, as claimed in claim 1, which enzymatic digestion step comprises digesting said bioadhesive protein with trypsin.

3. A method, as claimed in claim 1, which enzymatic digestion step comprises:
  (a) digesting said bioadhesive protein with clostridial collagenase; and
  (b) digesting the resultant collagenase-resistant fragment with trypsin.

4. A method for the preparation of decapeptides of the formula:

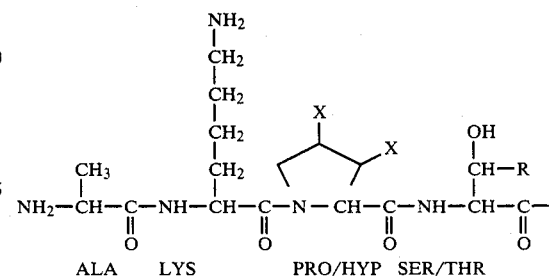

-continued

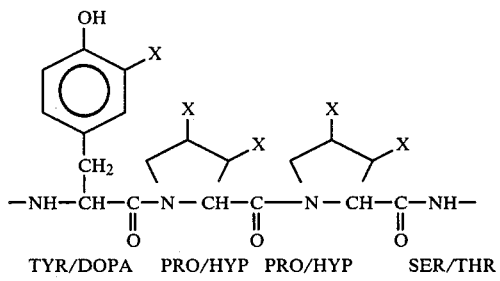
TYR/DOPA  PRO/HYP  PRO/HYP  SER/THR

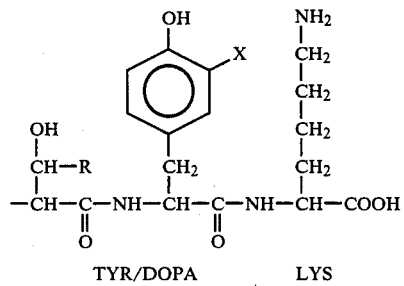
TYR/DOPA  LYS wherein each X is independently selected from the group consisting of hydroxyl and hydrogen, wherein each R is independently selected from the group consisting of hydrogen and methyl which comprises the steps of:

(a) isolating from marine mussels bioadhesive polyphenolic proteins which comprise:

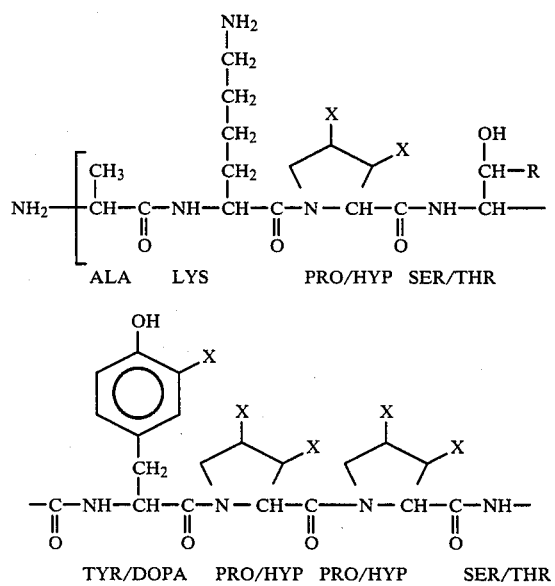
ALA  LYS  PRO/HYP  SER/THR

TYR/DOPA  PRO/HYP  PRO/HYP  SER/THR

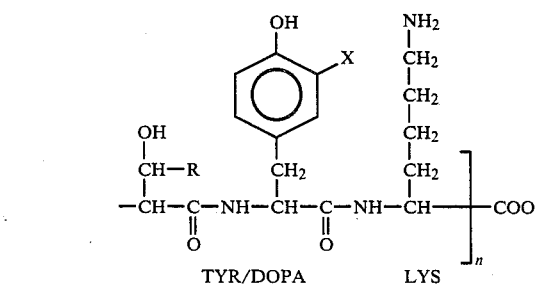
TYR/DOPA  LYS wherein n is a whole number from about 60 to about 100, wherein each X is independently selected from the group consisting of hydroxyl and hydrogen, and wherein each R is independently selected from the group consisting of hydrogen and methyl;

(b) digesting said bioadhesive proteins with clostridial collagenase;
(c) digesting the resultant collagenase-resistant fragment with trypsin; and
(d) recovering said decapeptides.

5. A method for the preparation of decapeptides of the formula:

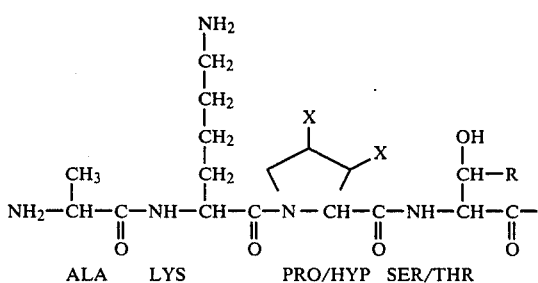
ALA  LYS  PRO/HYP  SER/THR

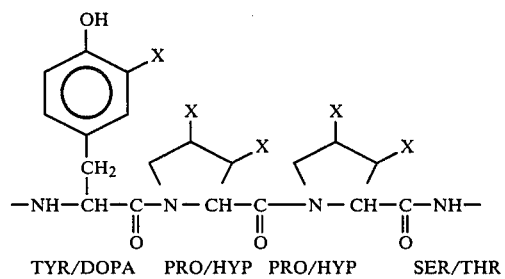
TYR/DOPA  PRO/HYP  PRO/HYP  SER/THR

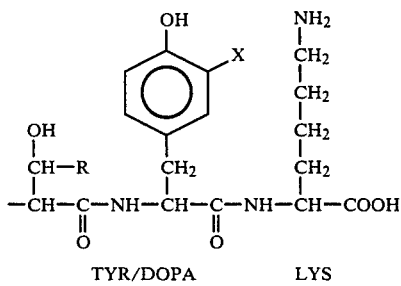
TYR/DOPA  LYS wherein each x is independently selected from the group consisting of hydroxyl and hydrogen, wherein each R is independently selected from the group consisting of hydrogen amd methyl which comprises the steps of:

(a) isolating from marine mussles bioadhesive polyphenolic proteins which comprise:

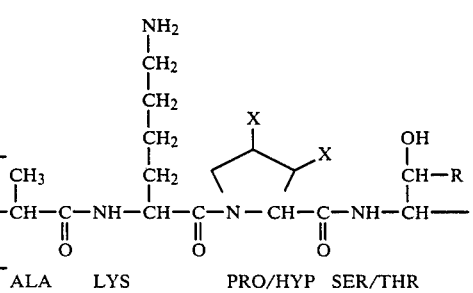
ALA  LYS  PRO/HYP  SER/THR

-continued

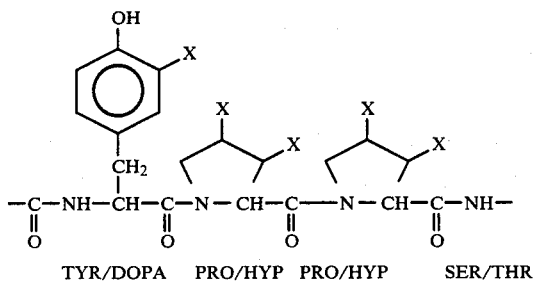

TYR/DOPA   PRO/HYP   PRO/HYP   SER/THR

-continued

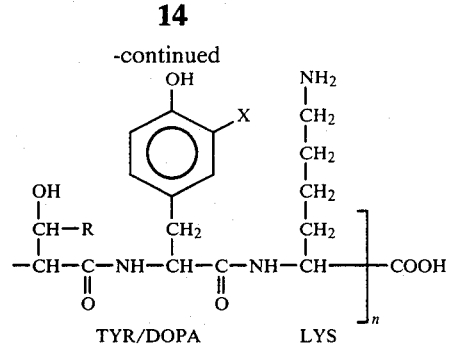

TYR/DOPA   LYS wherein n is a whole number from about 60 to about 100, and wherein each X is independently selected from the group consisting of hydroxyl and hydrogen, wherein each R is independently selected from the group consisting of hydrogen and methyl;

(b) digesting the bioadhesive proteins with trypsin; and (c) recovering said decapeptides.

6. A method, as claimed in claim 2, wherein the isolation of said bioadhesive proteins comprises the steps of:
a. disecting mussel phenol glands;
b. homogenizing said glands in neutral buffer;
c. centrifuging the resultant homogenized gland to a pellet;
d. homogenizing said pellet in cold-dilute acetic acid;
e. centrifuging said homogenized pellet; and
f. recovering the bioadhesive protein from the resultant supernatant.

* * * * *